United States Patent [19]

Relyea et al.

[11] Patent Number: 4,966,912
[45] Date of Patent: Oct. 30, 1990

[54] FUNGICIDAL 3-IMINO-1,4-OXATHIINS

[75] Inventors: Douglas I. Relyea, Bethany; Richard R. Regis, Torrington; Robert A. Davis, Cheshire, all of Conn.

[73] Assignee: Uniroyal Chemical Company, Inc., Middlebury, Conn.

[21] Appl. No.: 414,968

[22] Filed: Sep. 29, 1989

[51] Int. Cl.$^5$ .................... C07D 327/06; A01N 43/50
[52] U.S. Cl. .................................... 514/397; 548/336; 549/14; 514/433
[58] Field of Search .................... 514/397; 548/336

[56] References Cited

U.S. PATENT DOCUMENTS

| | | | |
|---|---|---|---|
| 3,249,499 | 5/1966 | von Schmeling et al. | 167/33 |
| 3,393,202 | 7/1968 | Kulka et al. | 260/327 |
| 4,152,334 | 5/1979 | Lee | 260/327 |

OTHER PUBLICATIONS

Phytopathology, vol. 57, No. 11, 1256–1257, Edington, L. V. and Barron, G. L.

*Primary Examiner*—Glennon H. Hollrah
*Assistant Examiner*—Patricia L. Morris
*Attorney, Agent, or Firm*—John A. Shedden

[57] ABSTRACT

This invention related to a novel class of 1,4-oxathiins bearing a substituted 3-imino group having a broad spectrum of fungicidal activity. The class of compounds is represented by formula (I):

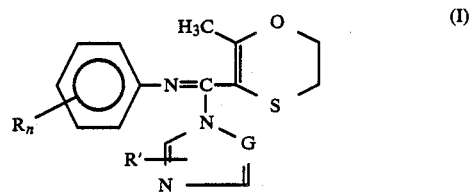

wherein:
$R_n$ is each independently $C_1$–$C_{12}$ linear or branched alkyl; halogen, trihalomethyl or $C_1$–$C_6$ alkoxy;
R' is hydrogen or $C_1$–$C_8$ linear or branched alkyl;
G is CH or N; and
n is 0, 1 or 2.

Fungicidal compositions, methods of controlling fungi and methods for preparing the compounds are within the scope of this invention.

6 Claims, No Drawings

FUNGICIDAL 3-IMINO-1,4-OXATHIINS

BACKGROUND OF THE INVENTION

1. Field of the Invention

The Present invention is directed to a novel class of 1,4-oxathiins bearing a substituted 3-amino group. More specifically, the present invention is directed to a novel class of substituted 1,4-oxathiins having a broader spectrum of fungicidal activity than known oxathiin fungicides.

2. Description of Related Art

The control of phytopathogenic fungi is of great economic importance since fungal growth on plants or on parts of plants, i.e., fruits, blossoms, foliage, stems, tubers, roots, inhibits production of foliage, fruit or seed and the overall quality of the harvested crop.

The 1,4-oxathiin 3-carboxanilides, for example, 5,6-dihydro-2-methyl-1,4-oxathiin-3-carboxanilide, are well known for their excellent control of phytopathogenic fungi of the order basidiomycetes, (hereinafter B), but are much less effective against fungal organisms of the classes phycomycetes, ascomycetes and imperfecti (hereinafter P, A and I respectively). Examples of disclosures of 1,4-oxathiin-3-carboxanilide can be found in U.S. Pat. Nos. 3,249,499; 3,393,202; and 4,152,334.

The continuous economic toll, discussed above, taken by fungi establish a continuing need to develop new, more effective fungicides which possess curative, preventative and systemic action to protect cultivated plants. Those requirements must be accomplished without any adverse side effects, caused by the fungicide, on the plants to be protected.

Surprisingly, the compounds of the instant invention although prepared from oxathiin carboxanilide intermediates, have been found to have a different spectrum of activity allowing effective control of economically important phytopathogens of the classes phycomycetes, ascomycetes, and imperfecti.

Accordingly, this invention provides a new class of compounds which exhibit an unexpectedly desirable degree of fungicidal activity and methods of preparing same.

This invention also provides novel fungicidal compositions comprising such substituted 1,4-oxathiins.

Additionally, this invention provides a method for controlling fungi employing such fungicidal compositions.

The above objects and other additional objects will become more fully apparent from the following description and accompanying Examples.

SUMMARY OF THE INVENTION

A novel class of 1,4-oxathiins bearing a substituted 3-imino group having a broader spectrum of fungicidal activity than known oxathiin fungicides; methods for preparing same; and fungicidally active compositions containing same are disclosed. The compounds are represented by the formula:

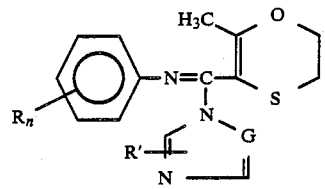

wherein
the substituents $R_n$, R', G and n are as hereinafter described.

DETAILED DESCRIPTION OF THE INVENTION

This invention relates to compounds of the formula:

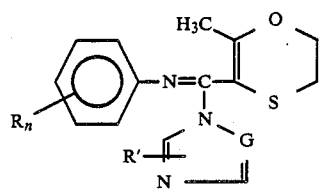

wherein:
$R_n$ is each independently $C_1$-$C_{12}$ linear or branched alkyl, halogen, trihalomethyl, or $C_1$-$C_6$ alkoxy;
R' is hydrogen or $C_1$-$C_8$ linear or branched alkyl;
G is CH or N;
n is 0, 1 or 2.
Preferably,
$R_n$ is halogen or $C_1$-$C_6$ alkoxy;
R' is hydrogen or $C_1$-$C_4$ linear or branched aklyl;
G is CH; and
n is 0 or 1.

In another aspect, this invention relates to fungicidal compositions comprising:
(A) a fungicidally effective amount of a compound having the structure of formula (I); and
(B) a suitable carrier In yet another aspect, this invention relates to a method of controlling fungi, which method comprises applying a fungicidally effective amount of a composition comprised of:
(A) a fungicidally effective amount of a compound having a structure in accordance with formula (I), and
(B) a suitable carrier.

In a further aspect, this invention relates to a process for preparing a compound of formula I which process comprises reacting a compound of the formula:

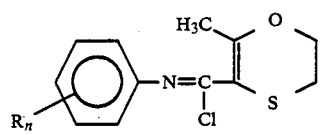

wherein $R_n$ is as defined above; with a compound of the formula:

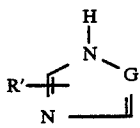

wherein R' and G are as defined in formula (I) above.

The compounds of formula (II) are readily prepared by reacting an appropriately substituted oxathiin carboxanilide of formula (IV):

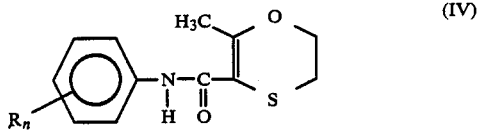

wherein:
R$_n$ is as defined above, with triphenylphosphine and carbon tetrachloride in acetonitrile.

Thus, it is possible to prepare the compounds of this invention by a sequence of two reactions which may be carried out in a single vessel.

The substituted oxathiin carboxanilide, triphenylphosphite and carbon tetrachloride are mixed together, preferably in the presence of acetonitrile and a 1,2,4-triazole is added. The reaction mixture exotherms and is stirred for 16 hours at room temperature. The solvents are removed by evaporation. The residue is treated with chloroform, and extracted with water. The residue obtained by evaporation of the chloroform is stirred with ethyl ether and filtered to remove triphenylphosphine oxide. The crude product after removal of the ether is purified by HPLC.

The compounds of formula (I) are useful in a process for controlling phytopathogenic fungi. In this process a fungicidally effective amount of the compound of formula (I) is applied to the locus under attack by said fungi.

In a first preferred embodiment, the method by which fungicidally effective amount of the comPound having structural formula (I) is applied to the plants to be protected from phytopathogenic fungi is by application of the compound to the foliage of the plants to be protected. This compound is applied to the foliage in a concentration of 0.125 to 10 kilograms per hectare (kg/ha); more preferably, from 0.125 to 5.0 kg/ha.

In the second preferred embodiment of the process for controlling phytopathogenic fungi, a fungicidally effective amount of the compound having the structural formula (I) is applied to the soil in which the plants to be protected from phytopathogenic fungi are grown. In this embodiment, the compound is applied to the soil at a concentration of 10 to 500 milligrams per liter (mg/1). The exact dosage, within this concentration range, is dictated by the fungi to be controlled and the particular plants to be protected.

The first preferred embodiment of the process for controlling fungi is known as the foliage method. The second preferred embodiment is known as the systemic method of application. Either method may be utilized prior to infection or after fungi attack has begun.

The compound having the structural formula (I) may be applied to seeds as a coating. This method provides plant protection from dangerous fungi by either chemotherapeutic means or systemic means or both. That is, the coating to the seed may protect the soil from infection by the fungi or may be taken up by the plant systemically to protect the plant from the fungal attack. In this seed coating method, the appropriate concentration of the compound is in the range of between 5 and 75 grams of compound per 100 kg. of seed.

The new fungicidal compositions of the present invention comprise a fungicidally effective amount of a compound of formula (I), and a carrier therefor.

The carrier employed in the fungicidal compositions may be a finely divided or granular organic or inorganic inert material. Among the inert carriers within the contemplation of this invention are attapulgate clay, sand, vermiculite, corncobs, activated carbon and mineral silicates such as mica, talc, pyrophyllite and clays.

In another preferred composition embodiment, the carrier comprises a solution. That is, the active agent, a compound of formula (I) is dissolved in a suitable solvent which acts as the carrier. Among the carrier solvents within the contemplation of this invention are acetone, methanol, isopropanol, t-butyl alcohol, cyclohexanone, toluene, xylene, dioxane, dimethylformamide, dimethylsulfoxide, ethylene dichloride, diacetone alcohol, and N-methylpyrrolidone.

In still another preferred carrier embodiment, the carrier comprises a water emulsion. The water emulsion is prepared from a solution as described immediately above. To the solution is added a surface active agent. Although well-known in the art, *McCutcheon's Detergents and Emulsifiers,* Allured Publishing Corp., Ridgewood, N.J. (1970); U.S. Pat. No. 2,514,916, Columns 2 to 4; and U.S. Pat. No. 2,547,734, Columns 3 and 4, provide detailed examples of such surface active agents. The surface active agents may be anionic, non-ionic or catonic.

In still another carrier embodiment, the carrier is a dispersant. In this embodiment, the active agent, i.e., the compound of formula (I), is mixed with a dispersant. The dispersant includes a solvent of the type described above, one of the above-described surface active agents and water. The active agent is dissolved in the solvent to form a solution and the solvent is dispersed in the water with the aid of the surface active agent.

In still another carrier embodiment, the active compound, formula (I), is premixed with an inert solid carrier which is added to a surface active agent and water to provide another form of dispersion type carrier.

As a variation of the last embodiment, the compositions of this invention may take the form of dust, granules or a paste of a wettable powder. In these embodiments, the active formula (I) is admixed with an inert solid carrier to form a solid composition. Thus, for example, in the embodiment wherein a powder is formed, the solid inert carrier is provided in powder form. In many such cases the inert carrier is a mineral silicate. The solid may be made wettable by the addition of a surface active agent well known to those skilled in the art and referred to in the above-recited references directed to surface active agent.

In a final carrier embodiment of the compositions of this invention, the carrier is an aerosol. To prepare an aerosol, the active compound is dissolved in a first solvent. This first solvent is conventional in the sense that although it is volatile it is not highly volatile. This solution is then admixed with a highly volatile solvent, a so-called liquid aerosol carrier. The aerosol carrier is liquid only under elevated pressure. At ordinary temperatures and at atmospheric pressure, the aerosol carrier is a gas. In a sub-embodiment of this preferred carrier, the aerosol carrier may itself be active. For example, the carrier may be an insecticide, a herbicide, a bactericide or the like.

Among the carriers discussed above, the carriers comprising solvents and emulsions are particularly preferred in the production of the fungicidal compositions of the present invention.

The following examples are given to illustrate the spirit of the present invention. Because these examples are given for illustrative purposes only, the invention embodied herein should not be limited to the actual examples provided.

EXAMPLE 1

Preparation of N-(2-methyl-1,4-oxathiin-3-yl-1,2,4-triazol-1-ylmethylene)benzenamine (Compound No. 2)

In a 50 mL three-necked flask equipped with magnetic stirrer, thermometer, and reflux condenser with drying tube were placed 3.30 g. (15 mmoles) of 2-methyl-3-phenylamino-arbonyl-1,4-oxathiin, 2.85 g. (41 mmoles) of 1,2,4-triazole, 7.03 g. (27 mmoles) of triphenylphosphine, 6.4 mL of carbon tetrachloride, and 6.4 mL of acetonitrile. Within 10 minutes an exotherm to 40° C. occurred. The mixture was then stirred 16 hours at room temperature. The solvents were removed by evaporation. The residue was dissolved in 50 mL of chloroform and extracted twice with 50 mL of water. The chloroform was removed by evaporation. The residue was stirred with 25 mL of ethyl ether and filtered to remove most of the triphenylphosphine oxide. Evaporation gave an oil which was purified by HPLC on a 6×30 cm. column of silical gel eluted with 50:50 ethyl acetate:hexane. After removal of the solvents there was obtained 2.73 g. (63.5% yield) of Compound 2, m.p. 84-86° C. The structure of the product was established by infrared and proton magnetic resonance spectrometry. The infrared absorption spectrum showed maxima as follows:

| 2925 cm.$^{-1}$ | $CH_3$ |
|---|---|
| 1620, 1640 | C = N |
| 1500, 1590 | C = C (aryl) |
| 1380, 1395 | $CH_3$ |
| 710, 775 | monosubstituted phenyl |

The proton nmr spectrum had the following resonances:
9.1 δ singlet; 1H triazole H-5;
8.1 singlet; 1H trizole H-3;
7.1-7.6 multiplet; 5H phenyl;
4.2-4.5 triplet; 2H $CH_2O$;
2.8-3.0 triplet; 2H $CH_2S$;
1.6 singlet; 3H methyl.

EXAMPLE 2

Preparation of 3-chloro-N-(2-methyl-1,4-oxathiin-3-yl-imidazol-1-ylmethylene)benzenamine (Compound 6)

In a 50 mL three-necked flask equipped with a magnetic stirrer, an inlet tube for dry nitrogen, a thermometer, and a reflux condenser with drying tube were placed 3.23 g. (12 mmoles) of 3-(3-chlorophenylaminocarbonyl)-2-methyl-1,4-oxathiin, 5.70 g. (22 mmoles) of triphenylphosphine, 5.2 mL of carbon tetrachloride, 5.2 mL of acetonitrile, and 2.23 g. (33 mmoles) of imidazole. The reaction mixture was stirred for sixteen hours under a slow stream of dry nitrogen without heating. The solvents were then removed by evaporation, replaced with 50 mL of chloroform, and the chloroform solution extracted twice with 50 mL of water. The residue obtained by evaporation of the chloroform was stirred with 25 mL of ethyl ether and filtered to remove triphenylphosphine oxide. The crude product remaining after removal of the ether was purified by HPLC on a 6×30 cm. column of silca gel eluted with 60:40 ethyl acetate:hexane. Evaporation of solvents gave a residue of 1.24 g. (32.4% yield) of compound 6, m.p 78-80° C.

The structure of the product is supported by the infrared absorption spectrum

| 2925 cm.$^{-1}$ | $CH_3$ |
|---|---|
| 1620, 1635 | C = N |
| 1515, 1585 | C = C (aryl) |
| 1380 | $CH_3$ |
| 695, 710, 770 | m-disubstituted phenyl |
| 790, 885 | | and confirmed by the proton nmr spectrum
8.2 singlet; 1H imidazole 2-H;
7.6 singlet; 1H imidazole 4-H;
6.9-7.3 multiplet 5H imidazole 5-H; plus substituted phenyl;
4.2-4.4 triplet; 2H $CH_2O$;
2.8-3.0 triplet; 2H $CH_2S$;
1.6 singlet; 3H $CH_3$.

EXAMPLE 3

Preparation of Compound Nos. 1, 3-5 and 7-18

Additional compounds (Nos. 1, 3-5 and 7-18) within the scope of this invention were prepared using essentially the procedures outlined above in Examples 1 and 2. The structures and melting points of these compounds are summarized in Table I below.

TABLE I

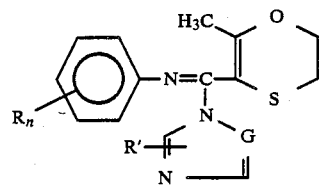
(I)

| Cpd. No. | R | R' | G | n | M.P. (°C.) |
|---|---|---|---|---|---|
| 1 | — | — | CH | 0 | 109-111 |
| 2 | — | — | N | 0 | 84-86 |
| 3 | — | 4-$CH_3$ | CH | 0 | oil |
| 4 | 4-$C_2H_5O$ | — | CH | 1 | 94-96 |
| 5 | 3-$CH_3O$ | — | CH | 1 | oil |
| 6 | 3-Cl | — | CH | 1 | 78-80 |
| 7 | 4-Cl | — | CH | 1 | 122-124 |
| 8 | 4-Cl | — | N | 1 | 103-105 |
| 9 | 4-$C_2H_5O$ | — | N | 1 | oil |
| 10 | 4-Br | — | CH | 1 | 108-111 |
| 11 | 4-Br | — | N | 1 | oil |
| 12 | 3-Cl | — | N | 1 | oil |
| 13 | 4-$C_2H_5O$ | 4-$CH_3$ | CH | 1 | oil |
| 14 | 3-Cl | 4-$CH_3$ | CH | 1 | oil |
| 15 | 4-Br | 4-$CH_3$ | CH | 1 | oil |
| 16 | 4-$C_2H_5O$ | 2-$CH_3$ | CH | 1 | 108-110 |
| 17 | 4-n-$C_4H_9$ | — | CH | 1 | oil |

TABLE I-continued $$\text{Structure (I)}$$

(Structure showing phenyl ring with $R_n$ substituent, connected via N=C to a ring system containing O, S, N, G, with $H_3C$ and $R'$ substituents)

| Cpd. No. | R | R' | G | n | M.P. (°C.) |
|---|---|---|---|---|---|
| 18 | 4-n-$C_{12}H_{25}$ | — | CH | 1 | oil |

Nuclear Magnetic Resonance (NMR) Data on Oils (δ, CDCl₃)

| Cpd. No. | |
|---|---|
| 3. | 1.60 (s,3H), 2.22 (s,3H), 2.70–3.05 (m,2H), 4.05–4.40 (m,2H), 6.70–7.45 (m,5H), 7.30 (s,1H), 7.95 (s,1H) |
| 5. | 1.65 (s,3H), 2.80–3.05 (m,2H), 3.75 (s,3H), 4.12–4.37 (m,2H), 6.50–6.80 (m,4H), 7.08 (s,1H), 7.58 (s,1H), 8.10 (s,1H) |
| 9. | 1.40 (t,3H), 1.60 (s,3H), 2.85–3.15 (m,2H), 4.05 (q,2H), 4.25–4.50 (m,2H), 7.05 (dd,4H), 8.10 (s,1H), 8.95 (s,1H) |
| 11. | 1.65 (s,3H), 2.85–3.10 (m,2H), 4.20–4.50 (m,2H), 7.30 (dd,4H), 8.18 (s,1H), 9.00 (s,1H) |
| 12. | 1.60 (s,3H), 2.90–3.15 (m,2H), 4.30–4.55 (m,2H), 6.95–7.45 (m,4H), 8.15 (s,1H), 8.95 (s,1H) |
| 13. | 1.40 (t,3H), 1.60 (s,3H), 2.25 (s,3H), 2.75–3.05 (m,2H), 4.00 (q,2H), 4.15–4.45 (m,2H), 6.90 (dd,4H) 7.27 (s,1H), 7.98 (s,1H) |
| 14. | 1.65 (s,3H), 2.25 (s,3H), 2.75–3.05 (m,2H), 4.15–4.45 (m,2H), 6.75–7.30 (m,4H), 7.30 (s,1H), 8.05 (s,1H) |
| 15. | 1.62 (s,3H), 2.25 (s,3H), 2.80–3.10 (m,2H), 4.15–4.50 (m,2H), 7.12 (dd,4H), 7.37 (s,1H), 8.10 (s,1H) |
| 17. | 0.95 (t,3H), 1.10–1.60 (m,4H), 1.60 (s,3H), 2.40–2.75 (m,2H), 2.80–3.05 (m,2H), 4.15–4.40 (m,2H), 6.85–7.50 (m,5H), 7.60 (s,1H), 8.15 (s,1H) |
| 18. | 0.50–1.45 (m,23H), 1.60 (s,3H), 2.15–2.55 (m,2H), 2.75–3.05 (m,2H), 4.10–4.40 (m,2H), 6.85–7.20 (m,5H), 7.60 (s,1H), 8.12 (s,1H) |

The following abbreviations and symbols are used to express the NMR data above: s = singlet; t = triplet; q = quartet; d = doublet; m = multiplet; δ - ppm relative to TMS and H = proton.

EXAMPLE 4

Preparation of Fungicidal Compositions

The compounds prepared in Examples 1-3 (Compound Nos. 1-18) were formed into compositions. This was accomplished by dissolving 0.3 grams of each of the compounds in 10 mL of acetone or other suitable inert solvent. Each of these solutions was treated with 1 to 2 drops of an emulsifying agent, such as Triton X-100, a trademark of Rohm & Haas for an octyl phenoxy polyethoxy ethanol, and water was added to form an emulsion. The degree of dilution with water was dictated by the desired concentration of the composition. The greater the quantity of water added the lower the concentration of the composition, reported in milligrams per liter (mg/L).

EXAMPLE 5

Control of Powdery Mildew Fungus (Systemic Root Uptake)

Each of the Compound Nos. 1-18 prepared in accordance with Examples 1-3 were tested to evaluate their effectiveness in preventing or controlling powdery mildew disease of barley caused by the fungus *Erysiphe graminis* (A) and powdery mildew disease of cucumber caused by the fungus, *Erysiphe cichoracearum* (A). This prevention or control capability was tested by utilizing the compounds of the present invention to control these diseases by systemic root uptake.

To accomplish this task, Pots (4×4×3.5 inches) containing 10 plants of barley (Variety "Herta") and cucumber (Variety "Marketmore 70") were grown to age 6 days and 10 days, respectively. Upon reaching these ages, 45 mL of emulsion compositions formed in accordance with Example 4 were added to each pot. That is, 48 pots were treated with emulsion compositions of the 18 compounds prepared in accordance with Examples 1-3. The 45 mL compositions saturated the soil without significant loss through drainage into the saucers below the pots. In addition, a number of pots containing the same barley and cucumber plants were left untreated. These pots were used as controls.

Twenty-four hours after the treatment with the compositions of the present invention, both the barley and cucumber plants in all the pots, those treated and those untreated, were inoculated with powderY mildew fungus. This was accomplished by tapping leaves of previously infected barley and cucumber plants over the treated and untreated pots containing the barley and cucumber plants, respectively, to distribute spores of the fungus over the plants tested.

Six days after inoculation, disease control was evaluated on a 0 to 6 rating scale. A 0 rating was assigned when no disease was evidenced and a 6 rating was given for severe disease. Intermediate ratings were assigned depending on the degree of disease. Percent control was computed by comparing the ratings for the treated and untreated plants.

The results of this example, that is, the percent control for each of the compounds tested is reported in Table II. The results of the powdery mildew disease control of barley is reported under the title of "BMS 250". The control of cucumber powdery mildew is similarly reported under the title of "CMS 250". It is noted that Table II appears after Example 9.

EXAMPLE 6

Control of Powdery Mildew in Barley by Foliar Application

Eight plants of "Larker" variety barley were planted in a pot. The number of pots were sufficient to accommodate testing in duplicate or triplicate pots for each of the 18 compounds tabulated in Table I. This number included a duplicate number of pots which acted as controls as will be discussed below.

Each of the compounds tabulated in Table I were tested by being sprayed onto the plants as compositions, prepared in accordance with Example 4 at an emulsion composition concentration of 1,000 mg/L. Compositions of each compound were sprayed on two or three pots. A number of pots were unsprayed and thus acted as controls. That is, for each pot sprayed, an unsprayed pot was utilized as a control.

After the leaves of the sprayed pots were dried, they and the unsprayed control pots were placed in a greenhouse maintained at 21° C. All the pots were then inoculated with barley powdery mildew fungus, *Erysiphe graminis* (A). This inoculation was accomplished by distributing spores of the fungus over the leaves to be tested from plants which had previously been infected with the mildew disease.

Five days after inoculation, the plants were evaluated and assigned a disease rating of 0 to 6 as described in Example 5. Again, percent control was computed by comparing the treatment scores with the scores of the untreated controls. The results of these tests are summarized in Table II under the title "BMP 1,000".

EXAMPLE 7

Control of Rice Blast Disease by Foliar Treatment

Five Bellemont rice plants each were grown in a plurality of pots. The number of pots with planted rice plants were sufficient to test the compositions of all compounds listed in Table I as well as controls therefor, the number of controls equal to the number of pots treated with each compound.

Three to four weeks after planting, the rice plants were sprayed with compositions of the compound of this invention, prepared in accordance with Example 4. The concentration of each composition was 1,000 mg/L. An equal number of pots, also containing five rice plants per pot, remained unsprayed.

Sprayed and unsprayed pots of the plant were inoculated with spores of the rice blast fungus, *Pyricularia oryzae* (I). This inoculation was accomplished by preparing inoculum containing 20,000 to 30,000 spores per milliliter. The inoculum so prepared was sprayed on the plants with 1 to 2 drops of Tween 20, a trademark of I.C.I. for a non-ionic surfactant (ethoxylated ethylene sorbitan monolaurate) to insure proper wetting of the inoculum onto the plant leaves.

The plants were incubated in a controlled chamber at a humidity of 99% and a temperature of 21° C for about 24 hours to allow infection to occur. The plants, after 24 hours in the control chamber, were transferred to a greenhouse for six days to permit disease development to occur. Disease was manifested by blast lesions on the leaves. Disease control was calculated by either counting lesions, if infection was moderate, or evaluating by the 0 to 6 rating system defined in Example 5. Of course, the evaluation system used in rating any of the compounds of the present invention was also utilized in evaluating its control. The results of this test are also tabulated in Table II under the title "RCB 1,000".

EXAMPLE 8

Control of Bean Rust Fungus Eradicant Test

Pots were planted with two pinto bean plants, *P. vulgaris* each, susceptible to rust disease. When the plants were 7 days old, at the primary leaf stage of growth, they were all sprayed with a suspension containing 20,000 spores of the bean rust fungus, *Uromyces phaseoli* (B), per mL. All the pots containing the plants were then incubated in a controlled environmental chamber, maintained at 99% humidity and 21° C, for 24 hours to allow infection to occur. The plants were then removed from the incubator and allowed to dry. Two days after inoculation the infected plants were sprayed with compositions formed from the compounds of this invention, set forth in Example 4, at a dosage of 1,000 mg/L. A number of infected plants were not sprayed and acted as controls. All of the sprayed and unsprayed plants were then placed in a greenhouse at 21° C. for five days to allow any disease present to be expressed.

All the plants sprayed with the sPore suspension were assessed for disease using the 0 to 6 rating system described in Example 5. Control of disease was determined by comparing treated plants with the untreated controls. The control of disease, expressed as percent reduction of disease, is included in Table II under the title "BRE 1,000".

EXAMPLE 9

Control of Nine Fungus Species

Compounds listed in Table I were solubilized in acetone at a concentration of 500 mg/L. That is, solutions were made of the compounds of the present invention such that there was 500 parts by weight of active compounds per million parts by volume of acetone. Filter paper discs, each 11 mm. diameter, were dipped in each of the test solutions. The discs were allowed to air dry to drive off the acetone solvent. A number of discs were treated to provide controls.

The treated and untreated discs were then placed on agar plates and 8 fungus species: *Alternaria solami* (ALT)(I), *Botrytis cinerea* (BOT)(I), *Fusarium oxysporum* (FUS)(I), *Helminthosporium maydis* (HMAY)(I), *Phytophthora infestans* (PHY)(P), *Erysiphe polgoni* (PMP)(A), *Sclerotinia sclerotiorum* (SCM)(A) and *Sclerotim rolfsii* (SCO)(I) were added to the center of each test disc in the form of a culture plug with the fungus mat in contact with the treated paper of the test disc. Two drops of a ninth fungi species, *Cercospora arachidicola* (CER)(I), were added as spore suspension (20,000 spores/mL) to the chemically treated test disc, rather than a mycelial culture plug. The plates were incubated at 29° C. in an oven and then the first eight fungus species were evaluated by measuring the radius from the center of the fungus colony of the untreated discs.

Percent growth inhibition of each of the compounds tested was determined as a function of the difference between the radii of the treated and untreated disc for these eight fungus species.

In the case of the *Cercospora arachidicola* (CER)(I) fungi, scoring was done on a numerical bases as follows:
100 = Complete inhibition of germination and growth.
80 = Nearly complete inhibition but some growth.
50 = Partial inhibition of growth or, early complete inhibition but later growth begins.
20 = Some inhibition of growth, but not significant.
0 = No inhibition of growth.

The results of all the above tests appear in Table II under the titles "ALT 500," "BOT 500," "FUS 500," "HMAY 500," "PHY 500," "PMP 1000," "SCM 500,""SCO 500" and "CER 500."

TABLE II

| | Percent Fungicidal Control | | | | | | | | | | | | | |
|---|---|---|---|---|---|---|---|---|---|---|---|---|---|---|
| | ALT | BMP | BMS | BOT | BRE | CER | CMS | FUS | HMAY | PHY | PMP | RCB | SCM | SCO |
| Cpd. | 500 | 1000 | 250 | 500 | 1000 | 500 | 250 | 500 | 500 | 500 | 1000 | 1000 | 500 | 500 |
| No. | Ex. 9 | Ex. 6 | Ex. 5 | Ex. 9 | Ex. 8 | Ex. 9 | Ex. 5 | Ex. 9 | Ex. 9 | Ex. 9 | Ex. 9 | Ex. 7 | Ex. 9 | Ex. 9 |
| 1 | 55 | 100 | 0 | 100 | 75 | 100 | 15 | 75 | 100 | 100 | 0 | 100 | 100 | 20 |
| 2 | 0 | 35 | 0 | 0 | 0 | 0 | 0 | 15 | 15 | 15 | 0 | 50 | 100 | 0 |
| 3 | 25 | 15 | 0 | 0 | 0 | 0 | 0 | 45 | 60 | 80 | 0 | 15 | 100 | 0 |
| 4 | 5 | 60 | 50 | 85 | 0 | 100 | 0 | 70 | 80 | 100 | 0 | 100 | 65 | 0 |

TABLE II-continued

| | Percent Fungicidal Control | | | | | | | | | | | | | |
|---|---|---|---|---|---|---|---|---|---|---|---|---|---|---|
| Cpd. No. | ALT 500 Ex. 9 | BMP 1000 Ex. 6 | BMS 250 Ex. 5 | BOT 500 Ex. 9 | BRE 1000 Ex. 8 | CER 500 Ex. 9 | CMS 250 Ex. 5 | FUS 500 Ex. 9 | HMAY 500 Ex. 9 | PHY 500 Ex. 9 | PMP 1000 Ex. 9 | RCB 1000 Ex. 7 | SCM 500 Ex. 9 | SCO 500 Ex. 9 |
| 5 | 95 | 0 | 35 | 50 | 0 | 100 | 0 | 90 | 100 | 100 | 0 | 100 | 100 | 0 |
| 6 | 65 | 20 | 15 | 100 | 0 | 100 | 0 | 85 | 90 | 100 | 0 | 100 | 60 | 0 |
| 7 | 85 | 60 | 15 | 100 | 0 | 100 | 0 | 100 | 100 | 100 | 0 | 100 | 40 | 0 |
| 8 | 0 | 0 | 0 | 0 | 0 | 0 | 20 | 0 | 0 | 45 | 0 | 0 | 70 | 35 |
| 9 | 0 | 35 | 0 | 10 | 0 | 0 | 60 | 15 | 30 | 85 | 0 | 15 | 75 | 0 |
| 10 | 100 | 0 | 0 | 100 | 0 | 100 | 0 | 100 | 100 | 100 | 0 | 35 | 50 | 35 |
| 11 | 0 | 50 | 0 | 45 | 0 | 0 | 0 | 10 | 0 | 70 | 0 | 0 | 30 | 35 |
| 12 | 0 | 35 | 0 | 0 | 0 | 0 | 0 | 0 | 0 | 65 | 0 | 0 | 100 | 0 |
| 13 | 60 | 60 | 35 | 5 | 0 | 100 | 0 | 50 | 50 | 75 | 0 | 0 | 75 | 0 |
| 14 | 65 | 0 | 0 | 20 | 0 | 100 | 0 | 65 | 40 | 100 | 0 | 35 | 50 | 0 |
| 15 | 65 | 40 | 0 | 100 | 0 | 100 | 0 | 80 | 50 | 100 | 0 | 50 | 30 | 50 |
| 16 | 60 | 15 | 0 | 100 | 0 | 0 | 0 | 5 | 75 | 45 | 0 | 0 | 100 | 25 |
| 17 | 65 | 85 | 50 | 10 | 0 | 100 | 0 | 40 | 85 | 90 | 0 | 75 | 80 | 0 |
| 18 | 10 | 85 | 35 | 20 | 0 | 0 | 25 | 15 | 20 | 15 | 0 | 100 | 0 | 0 |

EXAMPLE 10

Comparative Examples

Comparative tests using the procedures heretofore described, were performed with compounds analogous to those of the instant invention to determine the biological efficacy of the analogue The compound and associated results are reported in Table III. These compounds are outside the scope of this invention.

TABLE III

| Comparative Compound | ALT 500 | FUS 500 | BMS 250 | BRE 1000 | PMP 1000 | RCB 1000 | SCM 500 |
|---|---|---|---|---|---|---|---|
| (Ph-CH(N-N=CH-N)-C(O)-Ph) | 5 | 0 | — | 0 | 0 | — | 10 |
| (Ph-C(N-CH=CH-N)=N-Ph) | 20 | 55 | 25 | 0 | 0 | — | 20 |
| (Ph-C(N-CH=CH-N)=N-SO$_2$-Ph) | 0 | 0 | 0 | 0 | 0 | — | 0 |
| (Ph-C(Ph)=N-NH-Ph) | — | — | — | 0 | — | — | — |

We claim:

1. A compound of formula I:

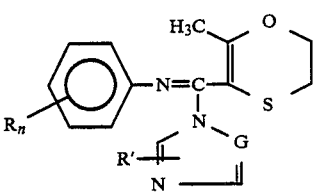

wherein:
$R_n$ is each independently $C_1$-$C_{12}$ linear or branched alkyl, halogen, trihalomethyl or $C_1$-$C_6$ alkoxy;
R' is hydrogen or $C_1$-$C_8$ linear or branched alkyl;
G is CH and
n is 0, 1 or 2.

2. A compound of claim 1 wherein:
$R_n$ is halogen or $C_1$-$C_6$ alkoxy;
$R'$ is hydrogen or $C_1$-$C_4$ linear or branched alkyl;
G is CH; and
n is 0 or 1.

3. A fungicidal composition comprising:
(a.) a fungicidally effective amount of a compound of claim 1; and
(b.) a suitable carrier.

4. A fungicidal composition comprising:
(a.) a fungicidally effective amount of a compound of claim 2; and
(b.) a suitable carrier.

5. A method of controlling fungi which comprises applying thereto an effective amount of a compound of claim 1.

6. A method of controlling fungi which comprises applying thereto an effective amount of a compound of claim 2.

* * * * *